US009658139B2

(12) United States Patent
Hering et al.

(10) Patent No.: US 9,658,139 B2
(45) Date of Patent: May 23, 2017

(54) SYSTEM AND METHOD FOR THE CONCENTRATED COLLECTION OF AIRBORNE PARTICLES

(71) Applicant: TSI Incorporated, Shoreview, MN (US)

(72) Inventors: Susanne V. Hering, Berkeley, CA (US); Gregory S. Lewis, Berkeley, CA (US); Arantzazu Eiguren Fernandez, El Cerrito, CA (US); Frederick Quant, Shoreview, MN (US); Kenneth R. Farmer, II, Lake Elmo, MN (US)

(73) Assignees: TSI INCORPORATED, Shoreview, MN (US); AEROSOL DYNAMICS INC., Berkley, CA (US)

( * ) Notice: Subject to any disclaimer, the term of this patent is extended or adjusted under 35 U.S.C. 154(b) by 399 days.

(21) Appl. No.: 14/012,818

(22) Filed: Aug. 28, 2013

(65) Prior Publication Data

US 2014/0060155 A1 Mar. 6, 2014

Related U.S. Application Data

(60) Provisional application No. 61/695,818, filed on Aug. 31, 2012.

(51) Int. Cl.
*G01N 15/00* (2006.01)
*G01N 1/22* (2006.01)
*G01N 15/06* (2006.01)

(52) U.S. Cl.
CPC ......... *G01N 1/2202* (2013.01); *G01N 1/2208* (2013.01); *G01N 1/2211* (2013.01); *G01N 15/065* (2013.01); *G01N 2001/2217* (2013.01)

(58) Field of Classification Search
CPC ............... G01N 15/0266; G01N 15/02; G01N 15/0205; G01N 2001/2223; G01N 15/0656
USPC ........................................................ 73/865.5
See application file for complete search history.

(56) References Cited

U.S. PATENT DOCUMENTS 5,085,500 A * 2/1992 Blesener ................ G01N 21/53 250/574
5,118,959 A * 6/1992 Caldow ................ G01N 15/065 250/573
5,262,841 A * 11/1993 Blesener ................ G01N 21/53 250/574
6,230,572 B1 * 5/2001 Pui ......................... B82Y 15/00 73/863.21
6,544,484 B1 * 4/2003 Kaufman ........... G01N 15/0266 422/186
6,712,881 B2 3/2004 Hering et al.
7,029,921 B2 4/2006 Lee et al.
7,736,421 B2 6/2010 Hering et al.
7,796,727 B1 * 9/2010 Kaufman .................. H05F 3/06 378/64
8,192,523 B1 * 6/2012 Kaufman ................ B03C 3/017 128/200.24
8,349,582 B2 1/2013 Wu et al.

(Continued)

*Primary Examiner* — Eric S McCall
*Assistant Examiner* — Mohammed E Keramet-Amircolai
(74) *Attorney, Agent, or Firm* — Kagan Binder, PLLC

(57) ABSTRACT

A system and a method is described herein for the collection of small particles in a concentrated manner, whereby particles are deposited onto a solid surface or collected into a volume of liquid. The collected samples readily interface to any of a number of different elemental, chemical, or biological or other analysis techniques.

36 Claims, 14 Drawing Sheets

(56) References Cited

U.S. PATENT DOCUMENTS

| | | | | |
|---|---|---|---|---|
| 2002/0134137 | A1* | 9/2002 | Ondov | G01N 1/2273<br>73/28.05 |
| 2004/0020362 | A1* | 2/2004 | Hering | G01N 15/065<br>95/228 |
| 2005/0172735 | A1* | 8/2005 | Booker | G01N 15/06<br>73/865.5 |
| 2008/0083274 | A1* | 4/2008 | Hering | G01N 15/065<br>73/170.19 |
| 2012/0048112 | A1* | 3/2012 | Hering | B01D 5/0009<br>95/228 |
| 2013/0001137 | A1 | 1/2013 | Pelton et al. | |

* cited by examiner

SYSTEM AND METHOD FOR THE CONCENTRATED COLLECTION OF AIRBORNE PARTICLES

CROSS-REFERENCE TO RELATED APPLICATIONS

The present application claims priority to U.S. Provisional Patent Application No. 61/695,818, filed Aug. 31, 2012, entitled "System and Method for The Concentrated Collection of Airborne Particles," which is incorporated by reference herein in its entirety.

GOVERNMENT RIGHTS

This invention was made with government support under ES014997 and ES019081 awarded by National Institutes of Health and under NBCHC070117 awarded by Department of Homeland Security. The government has certain rights in the invention.

BACKGROUND OF THE INVENTION

Airborne particles below 2.5 μm in diameter, $PM_{2.5}$, are associated with increased morbidity and mortality. This same size class of particles also influences global climate, through absorption and scattering of light and through effects on the formation, albedo and lifetime of clouds. The smallest of these particles, below about 100 nm in diameter are associated with the emerging field of nanotechnology, and the occupational health risks associated with manufacturing and using nano materials.

Time-resolved information on the chemical, biological and elemental composition of the fine, airborne particles found in the atmosphere is needed to understand their sources, their impact on public health, and their role in global climate. In industrial environments, similar time-resolved compositional information is needed to protect worker health, to understand and monitor industrial processes.

There is a paucity of daily, time-resolved composition data for atmospheric particles. While gaseous pollutants such as ozone are measured continuously at 1200 sites throughout the country, atmospheric particle chemistry data are incomplete, generally limited to 24-hour averages once every third or sixth day, with just 380 sites nationwide. Complete data sets, with daily measurements, are needed for epidemiology studies. Sub-daily time resolution is critical to understanding sources, transport and transformation, and to evaluating exposure. Yet to date, such measurements are too costly for wide-spread deployment, nor is current technology appropriate for time-resolved personal or micro-environmental measurements. Moreover, in the field of industrial hygiene particle measurements are generally limited to gravimetric assays on integrated, 8-hour filter collection. Time-resolved chemical composition information is not readily available for worker protection. Accordingly, instruments that can provide concentrated, sequential collection of airborne particles are expected to provide useful assessments of health risks due to inhalation of atmospheric particles, and of nanoparticle exposure in the workplace, as well as tools to better assess the role of atmospheric particles in global radiation balance.

SUMMARY OF THE INVENTION

A system and a method are described herein for the collection of fine, submicrometer and nanometer sized particles, such as particles ranging from 7 nm to 2.5 μm in a concentrated manner, whereby particles are deposited onto a solid surface as a sub-millimeter spot, or collected into a volume of liquid. The collected samples readily interface to any of a number of different elemental, chemical, or biological or other analysis techniques.

In another example embodiment, a particle collection method collects sequential, "ready-to-analyze" airborne particle samples whereby particles are deposited within a set of microwells on a single collection plate or surface (or substrate or wafer or any other collection device or member) that can be analyzed automatically through any number of standard analytical techniques including, but not limited to, ion chromatography, high pressure liquid chromatography, gas chromatography, mass spectrometry or Laser Induced Breakdown Spectroscopy (LIBS). In a second related embodiment, the collection method deposits airborne particles directly into a water- or liquid-filled reservoir. This may be either a flowing stream, or it may be a batch method that provides sequential samples into separate aliquots for downstream analysis.

In a third example embodiment, the collection method is interfaced to an on-line analytical instrument to provide near real time analysis. Additionally, sample collection information can be coded directly onto the collection plate or surface, or collection vial, thereby simplifying the chain of custody and reducing sample and data handling. In yet further embodiments, the method can be combined with other particle instrumentation to measure number or mass concentration or light scattering, or to collect a preselected subset of airborne particles, such as those of a specific size, in a specific size range, those that are hygroscopic, or those that act as cloud nuclei.

The various embodiments of the nanomaterial (and submicrometer) collection technology taught herein utilize the laminar flow water condensation technologies of U.S. Pat. No. 6,712,881, or U.S. Pat. No. 7,736,421 (Ser. No. 11/868,163) and US Patent Pub. No. 2012/0048112 (Ser. No. 13/218,393), which are incorporated herein by reference in their entireties. These technologies enlarge particles through condensation of water vapor in a laminar flow whereby the supersaturation necessary for activation of condensation onto submicrometer and nanometer particles is created by passing the air sample through a passage with wetted walls, a portion of which is warmer than the flow. Specifically, all particles from about a few nanometers to about a few micrometers in diameter are grown to form a supermicrometer sized droplet. These droplets are sufficiently large to be readily captured by inertial means. Moreover, there is no bounce, or rebound, during the collection because of the inherent inelasticity of the droplets, providing high collection efficiencies. In contrast to the Particle into Liquid Sampler (U.S. Pat. No. 7,029,921), there is no need for steam injection, and the temperature of the air being sampled is well controlled throughout the process.

In one example embodiment, a particle collection system is provided that includes a particle growth assembly having interior wetted walls and configured to receive an aerosol flow, the particle growth assembly including a condensing vapor having a vapor pressure at the interior walls which is near saturation, wherein the aerosol flow through the particle growth assembly is configured to be a laminar flow. The particle growth assembly includes a conditioning portion with a wetted interior wall configured to bring the aerosol flow to near saturation at a first temperature ($T_1$), and an initiator portion with a wetted interior wall operatively coupled to the conditioning portion and configured to provide supersaturation conditions at a second temperature ($T_2$) for the aerosol flow using the condensing vapor to initiate droplet growth, wherein the second temperature ($T_2$) is configured to be higher than the first temperature ($T_1$). The particle growth assembly further includes a equilibrator portion with a wetted interior wall operatively coupled to the initiator portion and configured to lower a dew point for the aerosol flow and maintain supersaturation conditions for the aerosol flow at a third temperature ($T_3$), wherein the third temperature ($T_3$) is configured to be lower than the second temperature ($T_2$). The collection system further includes means for collecting by inertia the enlarged particles disposed near an outlet of the particle growth assembly. In a related embodiment, an inlet is provided to the collection system for providing the aerosol flow at ambient temperature, wherein the ambient temperature and the first temperature of the particle growth assembly are independent of each other.

In another example embodiment, a method is provided for collecting and concentrating particles for use in characterizing such particles in an aerosol flow. The method includes the steps of introducing a particle laden flow at a first temperature into a condenser, and passing the flow through the condenser having a second temperature greater than the flow wherein a vapor pressure of a condensing vapor at walls of the condenser is near saturation, thereby enlarging the particles to be collected. The next step is to collect by inertia the enlarged particles. In this example embodiment, the condensing vapor is water and the flow through the condenser is laminar.

In a related example embodiment, a particle collection apparatus is provided that includes an inlet receiving an aerosol flow; and a condenser coupled to the inlet and receiving the aerosol flow at a first temperature, the condenser having interior walls provided at a second temperature higher than the first temperature and including a condensing vapor having a vapor pressure at the interior walls which is near saturation, wherein the flow through the condenser is configured to be a laminar flow. The collection apparatus also includes a means for collecting by inertia the enlarged particles disposed close to a condenser outlet. In a related embodiment, the collection apparatus also includes a preconditioner at the first temperature that is operatively coupled to the inlet, the preconditioner having an outlet operatively coupled to the condenser.

DETAILED DESCRIPTION OF PREFERRED EMBODIMENTS

Figure 1:
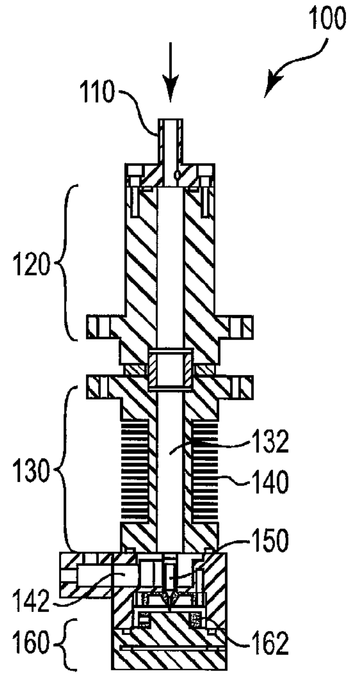
FIG. 1. is a low-flow, two-stage growth tube collector utilizing an impactor collector to form a concentrated, dry particle deposit in accordance with the present invention.

Following below are more detailed descriptions of various related concepts related to, and embodiments of, methods and apparatus according to the present disclosure for an improved system and method for characterizing particles in an aerosol flow for manufacturing applications including, but not limited to, pharmaceutical and semiconductor manufacturing, or for characterizing particles in indoor environments or the earth's atmosphere. It should be appreciated that various aspects of the subject matter introduced above and discussed in greater detail below may be implemented in any of numerous ways, as the subject matter is not limited to any particular manner of implementation.

In this example embodiment, a nanomaterial particle collection method that is disclosed here consists of two steps. First airborne particles are enlarged through water condensation in a predominantly laminar flow, as described by U.S. Pat. No. 6,712,881, U.S. Pat. No. 7,736,421 (Ser. No. 11/868,163) or US Patent Pub. No. 2012/0048112 (Ser. No. 13/218,393). In the second step, the droplets formed through condensational growth of the first step are collected by inertial means. This collection can be a dry or substantially dried deposit onto a solid surface (such as by impaction), or a wet deposit into a volume of water (such as by impingement). This example embodiment of the invention provides a collection of fine, submicrometer and nanometer sized particles in a concentrated manner, whereby particles are deposited onto a solid surface as a sub-millimeter spot, or collected into a volume of liquid. Several configurations of this approach are presented. In the examples provided herein, the material that condenses onto the particles is water, with air serving as the carrier gas. Yet, as noted in the referenced patents and publications and in this specification, this approach applies to any condensing vapor whose mass diffusivity is larger than the thermal diffusivity of the carrier gas.

In various example embodiments of the particle collection systems taught herein, a particle growth assembly is provided that is operatively coupled with a nozzle assembly or other means to facilitate the collection of particle samples through inertial means, such as impaction or impingement. Examples of inertia collection devices, such as impactors and cyclones, are disclosed in U.S. Pat. No. 8,349,582 which is incorporated herein by reference. The various embodiments described herein may also be adapted to include an optical component to count the droplets formed, and hence indicate, for example, the number concentration of particles, prior to their collection or the mass concentration if particle size and density are known.

One example embodiment of a particle collection method includes receiving an aerosol flow at ambient temperature and introducing same to a one-stage particle growth assembly such that the flow at ambient temperature $T_0$ is introduced directly into a condenser with interior walls that are wet and at a first temperature ($T_1$) such that $T_1>T_0$. In another example embodiment of a particle growth assembly (using an ambient-cold-hot approach) a conditioner is provided ahead of a one-stage condenser such that an aerosol flow at ambient temperature is introduced into the conditioner with interior walls at temperature $T_1$, which is operatively coupled to the condenser with walls at temperature $T_2$ throughout, where the walls of the conditioner and the condenser are wet, and $T_2>T_1$. An advantage to this design is that there is no restriction on the (relative) temperature of the conditioner ($T_1$) to that of the entering ambient flow ($T_0$) or to the temperature of any other flow.

In another embodiment of the particle growth assembly for the particle collection systems described herein, a particle growth assembly is provided using an "ambient-hot-cold" approach using a two-stage condenser such that an aerosol flow at ambient temperature $T_0$ is introduced directly into a condenser with interior walls that are wet, the first portion of which is at temperature $T_2$, wherein $T_2>T_0$, and a second portion of the condenser is at a temperature $T_3$, wherein $T_3<T_2$. Another example embodiment, using an "ambient-cold-hot-cold" approach, places a wet-walled conditioner at the beginning of the assembly to bring the ambient air flow to a high relative humidity at the desired temperature before entering the two-stage condenser component. With this approach flow at ambient (or inlet) temperature $T_0$ introduced into a conditioner with wetted interior walls at temperature $T_1$, followed by a two-part condenser with wetted walls at temperature $T_2$ followed by walls at temperature $T_3$, where $T_2>T_1$, and $T_3<T_2$. No restriction is placed on the temperature of the conditioner ($T_1$) relative to that of the entering flow ($T_0$), or on the entering flow temperature relative to $T_1$ and $T_3$.

Referring now to the Figures, FIG. 1 illustrates a collection device or apparatus 100 using the condensation (or condensational growth or particle growth) method of U.S. Pat. No. 6,712,881. A particle laden air flow enters via an inlet 110 that is coupled to a wet walled tube or conditioner 120, the first portion of which is colder than the second portion. The particle laden flow is under laminar conditions, i.e. the flow Reynolds number, defined as the ratio of the product of the flow velocity and tube diameter to the kinematic air viscosity, is less than 2000. In this example embodiment, the temperature of a first section or conditioner 120 is maintained somewhere between 2° C. and 20° C. In this example embodiment, the temperature of a second section or a condenser region 130 is set at a value between 20° C. and 40° C. warmer than the temperature of conditioner 120. As illustrated, the particle laden flow is downward (arrow), and the walls are wetted by means of a wick 140 which is in contact with a water reservoir 142. Other approaches for maintaining wetted walls are possible, such as by slowly dripping water onto the backside of the wick, and capturing the excess at the bottom. Conditioner section 120 brings the flow to near saturation at the desired temperature while growth region 130 is where droplets are formed (and enlarged) around the particles to be eventually collected. Within condenser region 130 heat and water vapor diffuse into the particle laden flow from the walls creating a region of water vapor supersaturation 132. The supersaturation activates the condensational growth onto small particles, whose equilibrium vapor pressure is elevated above that for a flat surface of the same temperature because of the energy associated with the surface, as described by the well-known Kelvin equation.

The sample aerosol flow then passes into an inertial collector assembly 160 via an impaction jet 150 for the capture of the enlarged particle droplets. In this example embodiment, inertial collector assembly 160 includes an impactor device consisting of a nozzle or jet 150 that directs the flow of enlarged droplets to a flat collection plate or substrate 162 located orthogonally to the axis of nozzle 150 as illustrated in FIG. 1. In various related example embodiments, inertial collector assembly 160 includes a small reservoir of liquid, or it may also be a cyclone assembly, whose walls can be maintained wetted by adjusting the temperature of the cyclone walls to induce the desired amount of condensation of water from the vapor phase. Because the droplets formed in condensation section 130 are several micrometers in diameter, the droplets are much more readily captured by inertial means than are the particles typical in ambient atmospheres.

In various related embodiments described herein, the collection plate or substrate (or vessel or bottle if a liquid is used as the collection method) is temperature controlled to assist in the collection process. For example, a heater may be used to dry the collection sample or a thermoelectric device can be used to maintain the collection sample in a range of temperatures. Further, in various related embodiments, the collection member or vessel is moved laterally or rotationally depending on how the user wants to displace or move the collected sample for analysis or storage. Hence, displacement systems include a stepper motor for rotational movement of a collected sample or lateral movement of the sample through another movement device.

Figure 2:
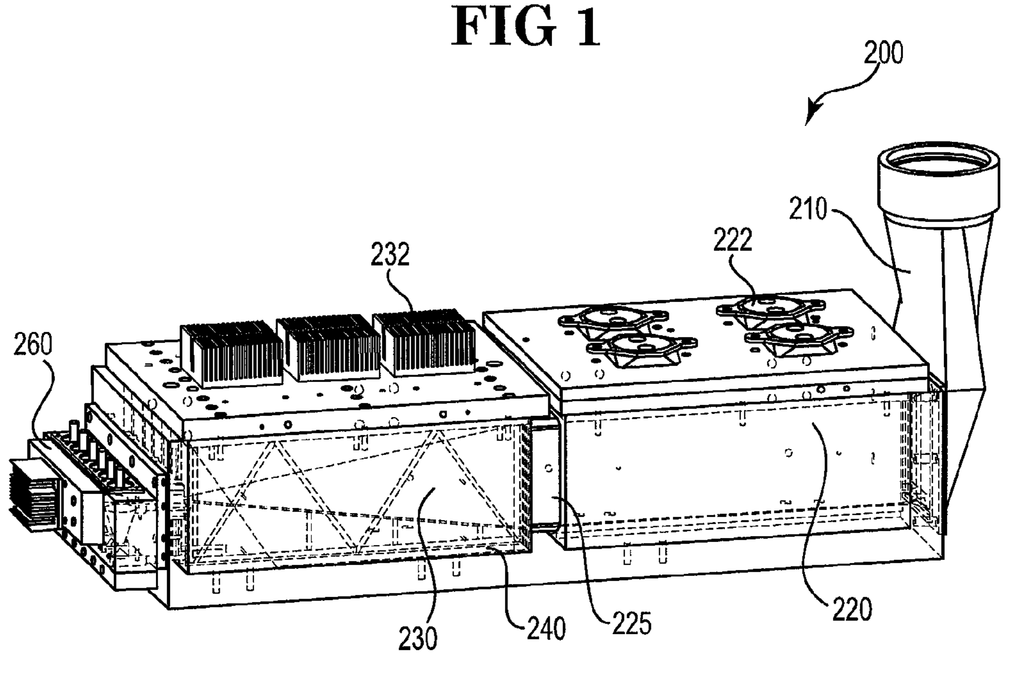
FIG. 2. is a high-flow, two stage growth system utilizing parallel plate geometry with cyclone collectors for collection into water in accordance with the present invention.

Referring now to FIG. 2, there is illustrated an example configuration of another collection device or apparatus 200 using a horizontal, parallel plate geometry with particle collection being directed into a wet-walled cyclone. This geometry has been used for sampling at high flow rates, of the order of 30 to 100 L/min. Apparatus 200 includes an inlet 210 coupled to a preconditioner 220 which is then coupled via an alignment insert 225 to a condenser 230 the outlet of which is coupled to a cyclone collector assembly 260. In this example embodiment, condenser 230 includes a wick reservoir assembly 240 for saturating the condenser with water vapor. As in FIG. 1, the condensation is achieved with two stage system wherein a conditioner (such as preconditioner 220) is followed by a warmer growth region (such as condenser 230). The walls of each channel are lined with a wick material (not illustrated but that forms part of wick assembly 240) that forms part of the lower portion of which is in contact with a water reservoir that extends along the bottom of the channels.

In this example embodiment, thermo-electric devices 222 are used to cool the first section. A liquid coolant removes waste heat from the thermo-electric devices and pumps this through channels within the walls of the growth region, thereby warming this section. The temperature of the growth region is controlled by cooling fins 232 (or fans) on the growth section. Other temperature regulation methods are possible. In this example embodiment, the inertial collector is a cyclone collector assembly 260, whose walls are wetted with condensate from the exiting flow. Water sheets along the wall of the cyclone, carrying with it the deposited particles to the collection cup at the bottom. Samples can be removed either periodically by extracting the accumulated liquid, such as with a syringe connected to a port within the cyclone. Alternatively, by using a syringe pump or other similar device, the sample can be removed continuously into a slow flow.

Figure 3A:
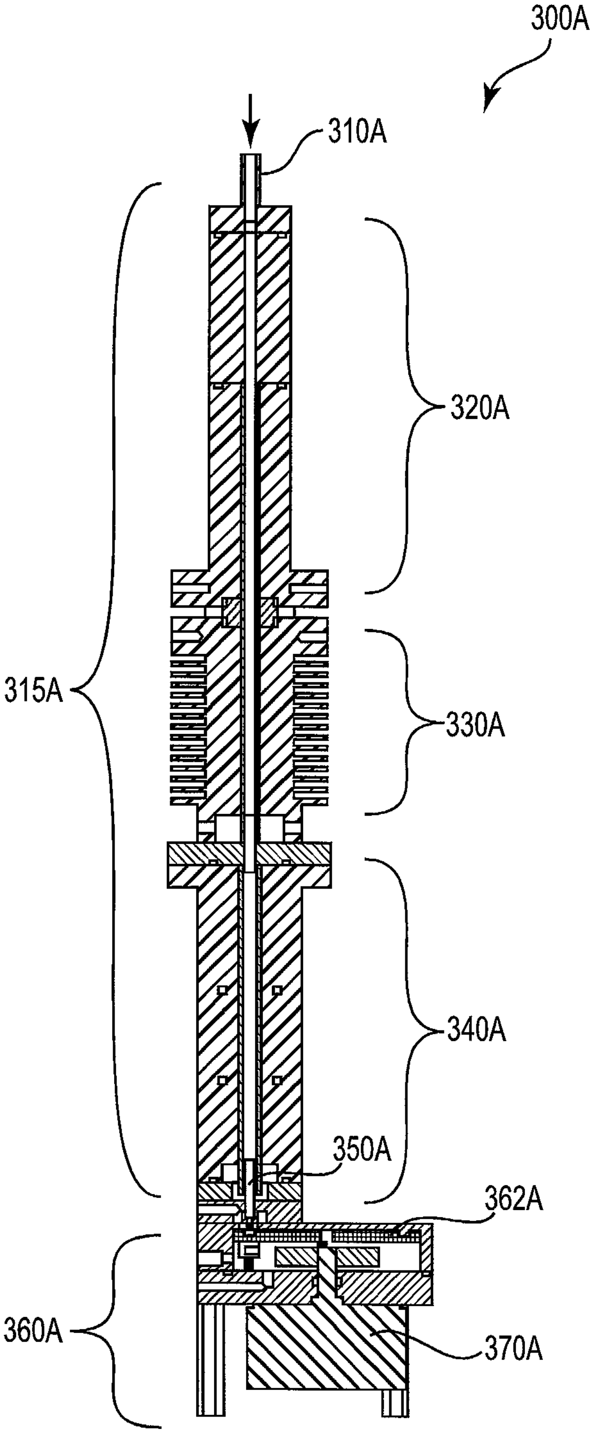
FIGS. 3A and 3B. are a three-stage growth tube collector for collection of sequential samples onto a multi-well plate and a three-stage growth tube collector for collecting a single sample, respectively, in accordance with the present invention.
Figure 3B:
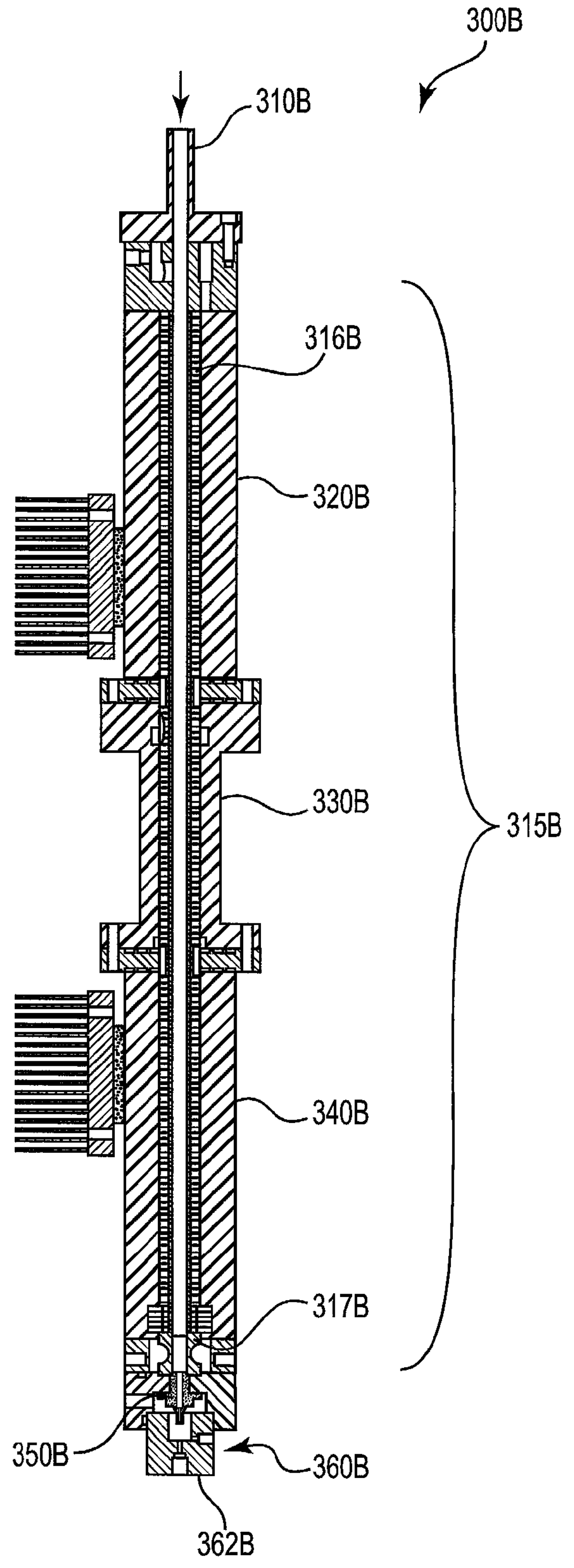

Referring now to FIGS. 3A-3B, there are illustrated example particle collection configurations of an apparatus 300A and 300B, also referred to as "smart samplers". These generally operate on the principle of "cold-hot-cold," wherein an ambient temperature could be an alternative embodiment provided at temperature $T_0$. In this approach a conditioner is provided ahead and coupled operatively with a two-stage particle growth assembly such that an aerosol flow is introduced into a conditioner with wetted interior walls at temperature $T_1$, thereafter operatively coupled to a particle growth assembly with wetted walls with two temperature regions, wherein a first region with walls at a temperature $T_2$ is followed by a second region with walls at a temperature $T_3$ wherein $T_2>T_1$, and $T_3<T_2$. An advantage to this approach is the reduction in the water vapor concentration and temperature of the flow at the point of collection. This is an important consideration for the collection of volatile constituents. A further advantage is that no restriction is placed on the temperature of the conditioner ($T_1$) relative to that of the entering flow ($T_0$), or on the temperature of $T_3$ relative to $T_1$.

Referring now to FIG. 3A, in this example embodiment, smart sampler 300A uses a three stage condensation method described in US Patent Pub. No. 2012/0048112 (Ser. No. 13/218,393). The airflow (arrow) passes through an inlet 310A and through a particle growth assembly 315A that includes a conditioner portion 320A and a second and third stages or portions referred to as an initiator portion 330A and a equilibrator portion 340A, respectively. Initiator portion 330A and equilibrator portion 340A are coupled co-linearly with conditioner portion 320A and represent and improvement to growth region 130 of FIG. 1. A nozzle assembly or jet 350A is operatively coupled to particle growth assembly 315A and is configured to direct the enlarged particles to a collector assembly 360A. In this example embodiment, the collection assembly is comprised of a collection plate 360A having a plurality of collection wells that is rotated annularly by a stepper motor 370.

In this example embodiment, initiator 330A is a short warm section that provides the water vapor to initiate the droplet growth (or particle condensational enlargement) and is at a temperature that is higher than the conditioner portion. In this example embodiment, the "equilibrator" lowers the dew point while maintaining the supersaturation conditions necessary for droplet growth and is at a temperature that is lower than the temperature of the initiator portion. The combined length of initiator 330A and equilibrator 340A sections is about the same as for the growth section described in U.S. Pat. No. 6,712,881. In this example embodiment, conditioner 320A is operated at between about 2° and about 20° C., initiator 330A walls are between about 20° C. and about 40° C. warmer than conditioner 320A, and equilibrator 340A is operated at between about 5° C. to and about 15° C. This three stage approach is advantageous when a lower temperature is desired for the collection. In the example embodiment illustrated, the overall length is about 120 mm, the tube diameter is about 8 mm and the sample flow rate may be varied from about 0.5 to about 1.6 L/min.

Once the particles are enlarged through condensational growth in any of the various above described embodiments, they are collected by inertial means (such as by impaction or impingement). In "smart sampler" 300A particles are deposited by impaction via nozzle 350 as sub-millimeter diameter, dry spots within sequential wells on a single collection plate or surface or substrate, such as substrate 162 or collection plate 362. Other collection options are possible, such as collection as a streak or set of spots on a flat surface, or direct deposition of the droplets into a small volume of water (such as by impingement). In smart sampler 300A, an acceleration nozzle 350A (see FIG. 3A) measuring about 0.8 to 2 mm is located at the exit of equilibrator 340A. A collection plate or surface is placed under nozzle 350A such that the active collection surface is approximately 5 mm (or 3 to 5 nozzle diameters) below the exit of the nozzle. The flow exiting equilibrator 340A accelerates through nozzle 350A centered above a small well and the droplet-encapsulated ambient particles are deposited by impaction on collection plate 362A. In this example embodiment, the nozzle is heated slightly to prevent condensation. A small heater, positioned under the active sample position (under collection plate 362A, for example) and kept between about 25° C. to about 30° C. and evaporates the water as the droplets are deposited, creating a dry collection spot.

Referring now to FIG. 3B, in this example embodiment, another smart sampler 300B uses a variation of the three stage condensation method described in US Patent Pub. No. 2012/0048112 (Ser. No. 13/218,393). The airflow (arrow) passes through an inlet 310B and through a particle growth assembly 315B that includes a conditioner portion 320B and a second and third stages or portions referred to as an initiator portion 330B and a equilibrator portion 340B, respectively. Initiator portion 330B and equilibrator portion 340B are coupled co-linearly with conditioner portion 320B. A nozzle assembly or jet 350B is operatively coupled to particle growth assembly 315B and is configured to direct the enlarged particles to a collector assembly 360. In this example embodiment, the collection assembly is comprised of a single well collection plate 360B. Smart sampler 300B includes a single wick 316B for generating the saturation conditions within particle growth assembly 315B that spans all three temperature regions (cold-hot-cold) of particle growth assembly 315B and that has a length of about 330 mm. The water (condensing vapor in this example) for maintaining the wetted wick is injected at the top of initiator portion 330B (with the warmest temperature). The inner diameter of the tube within particle growth assembly 315B lined by wick 316B is about 5 mm, so as to provide consistent particle growth over a wide range of particle concentrations (as described in US Patent Pub. No. 2012/0048112). Excess water is removed from the bottom, where wick 316B sits on a short (–30 mm) standpipe 317B. This approach eliminates the water fill reservoir, thereby minimizing the opportunities for accidental flooding.

Figure 4A:
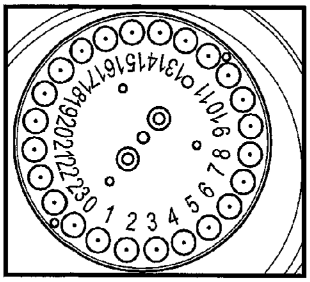
FIGS. 4A-4B. are multi-well collection plates showing black deposits formed from sampling an urban atmosphere with each deposit corresponding to one hour of sampling in accordance with the present invention.
Figure 4B:
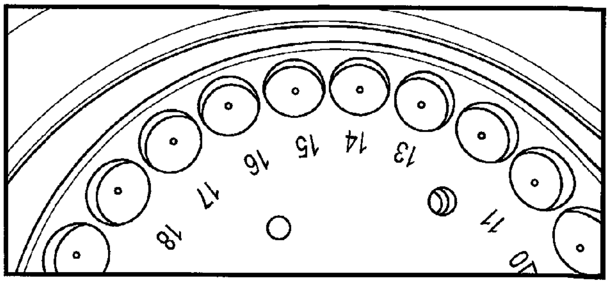

The collection surface, in another example embodiment, is tailored to the analytical method planned for the chemical or elemental analysis of the sample. When the planned analysis requires liquid extraction of the sample, such as high pressure liquid chromatography or ion chromatography, the collection plate or surface is designed to contain multiple wells, as illustrated in FIGS. 4A-4B. In this example embodiment, each well is about 6 mm in diameter, 2 mm deep, and located in a circle near the periphery of the plate or surface. Other configurations, such as an x-y grid, are possible. At the end of the desired collection period the plate or surface is moved by a displacement system or mechanism, such as a stepper motor. In this example embodiment, the collection plate is rotated by means of a stepper motor 370 to advance to the next well, providing a series of sequential collection deposits. A Teflon® gasket placed above the ring of sample wells shields all but the well that is under the impaction jet (such as nozzle 150 or 350), providing protection from the air stream after collection. As only the active well is heated, the samples can be stored cool.

In one example embodiment, a collection plate or surface is optionally outfitted with an embedded flash memory, or other recording or tracking device or system to encode the wafer (or plate or surface) ID and critical sample collection data for each well, such as location, start date and time, duration, air flow volume and data collection flags. This may be accomplished through an RF-ID tag that allows recording of the information without direct physical contact with the collection plate. The sample wafer (or plate or surface) may also be encoded with an optical tag, or bar code, which can be read by an appropriate device once the wafer is removed from the collector. For off-line analysis, the sample collection wafer is placed in a petri dish or other sealed storage container for storage prior to analysis. By using an RF-ID tag or optically scan-able code, the critical sample information can be read with a hand-held device from the collection wafer without opening the storage container.

Additionally, with appropriate hardware and software the wafer identification and sample information can be read by the analytical system. For example, the autosampler connected to a liquid, ion or gas chromatograph can be programmed to read the data and enter this information into the sample sequence information, such that the critical sample collection data, with date, time, location and volume of air sampled, is carried along in the same data sequence as the analytical data the provides a mass of analyte collected, from which the airborne concentration in mass of analyte per unit volume of air (typically expressed as μg/m3) can be calculated. This approach keeps the critical sample collection information with the sample; it automates the integration of the field sample collection information with the chemical or elemental analysis; it provides for an automated chain of custody, and greatly reduces the quality assurance and quality control steps necessary for accurate data collection.

Figure 5:
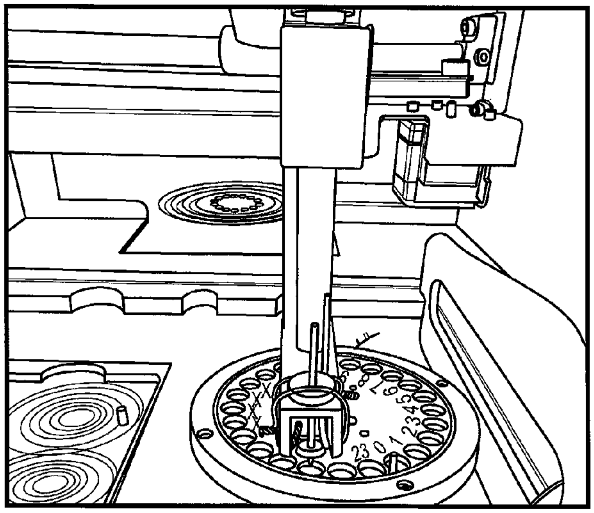
FIG. 5. is an interface of the collection plate or surface to a needle "prep and load" autosampler using TTL logic output to rotate the collection plate or surface in accordance with the present invention.

After sample collection, the deposits on the collection wafer (or plate or surface) can be analyzed in the laboratory using any of a number of analytical techniques. For those techniques designed for samples extracted into a liquid, such as ion chromatography, high pressure liquid chromatography, gas chromatography, or mass spectrometry, the wafer is placed in a standard needle "prep and load" autosampler as illustrated in FIG. 5. These autosamplers can be programmed to sequentially extract and analyze each of the deposits contained within the collection wafer automatically. Sample extraction is accomplished by using the needle autosampler to add extraction solution, waiting for a soak time, optionally subjecting it to an ultrasonic treatment, and then injecting. By adding an internal standard to the extraction solution, correction can be made for evaporative losses from the well. Typically the soak period occurs during the chromatographic run of the prior one or two samples, and thus the total time for analysis is that which is required for the chromatography. To access the various wells the autosampler needle position can be programmed to the position of each well, or its TTL logic output can be used to activate a small motor that rotates the wells under a fixed needle position. In this manner the autosampler handles the interface for the analysis, with a single system extracting and analyzing all of the sample deposits in the plate or surface without operator intervention. This eliminates the manual handling currently required for the extraction and analysis of individual filter samples.

Other analysis methods are possible. For example, the individual collection spots, such as the samples collected by collection plate 362, may be analyzed directly through methods such as laser ablation such as by Laser Induced Breakdown Spectroscopy (LIBS). The collection method allows any material for the collection surface, and thus the substrate used for collection to be tailored to the analytical method. For example, aluminum can be used when carbon analysis is desired or nylon can be used for analysis of trace metals.

With any of the smart sampler collection plates or surfaces (or wafers or substrates), it is possible to provide for a flash memory or other encoding method whereby the critical sample information such as location, sample date, sample start time, sample duration, sampled air volume, and system status flags, are recorded on the plate or surface for each collection well or spot. With an appropriate interface, these analytical systems can be programmed to combine analytical results with the sample collection data to produce an immediate, reduced data set. Enabled by the concentrated manner in which the particle sample is deposited, the smart sampler approach eliminates filter handling, keeps the critical information with the sample, and enables the laboratory steps to be more fully automated.

Figure 6:
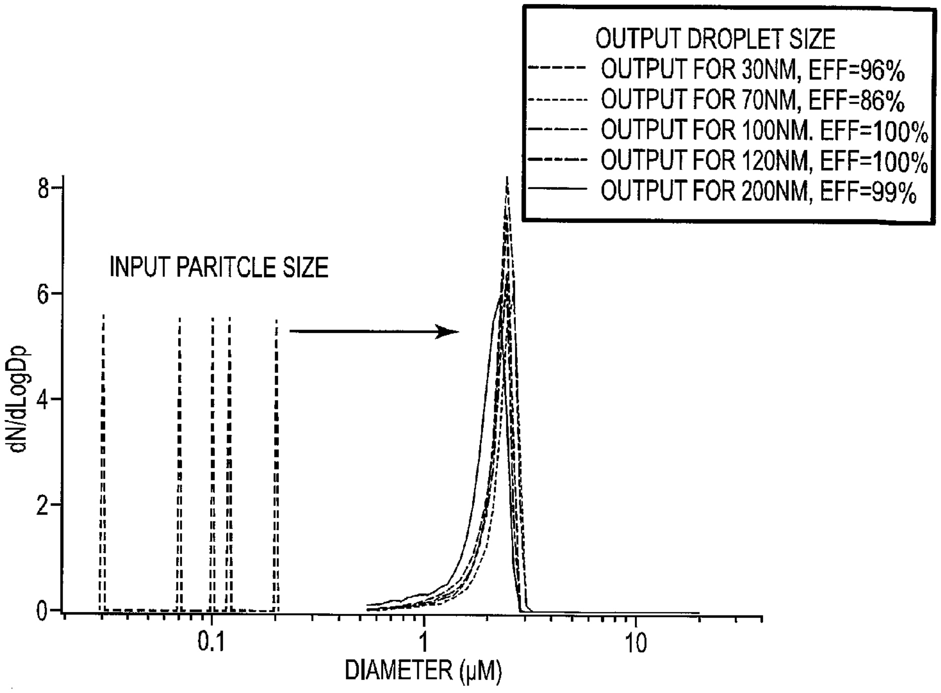
FIG. 6. is a graph illustrating the size distribution of droplets exiting growth tube when sampling particles of varying sizes ranging from 30 nm to 200 nm in accordance with the present invention.

For each of the nanomaterial particle collectors described above, each of which provides a concentrated particle deposit or collection, an advantage is the condensational growth of the nanometer and submicrometer particles. Once the particles are grown, they are much more readily collected by inertial means. As illustrated in FIG. 6, there is illustrated the size distribution of droplets formed when sampling monodisperse fractions of ambient particles selected by differential mobility analysis. FIG. 6 combines results for several runs when the selected size was varied from 30 nm on up to 120 nm. The data corresponds to a two-stage system similar to that of FIG. 1, with a conditioner temperature of 5° C. and a condenser temperature of 25° C. As evidenced by the data, the droplets formed from these particles are all in the 1 to 3 μm, size range, independent of the size of the particle that was sampled. As is well known, inertial collection is much more easily accomplished for particles that are a few micrometers in diameter, than for the sub-300 rim sizes that characterize most ambient particles.

Figure 7:
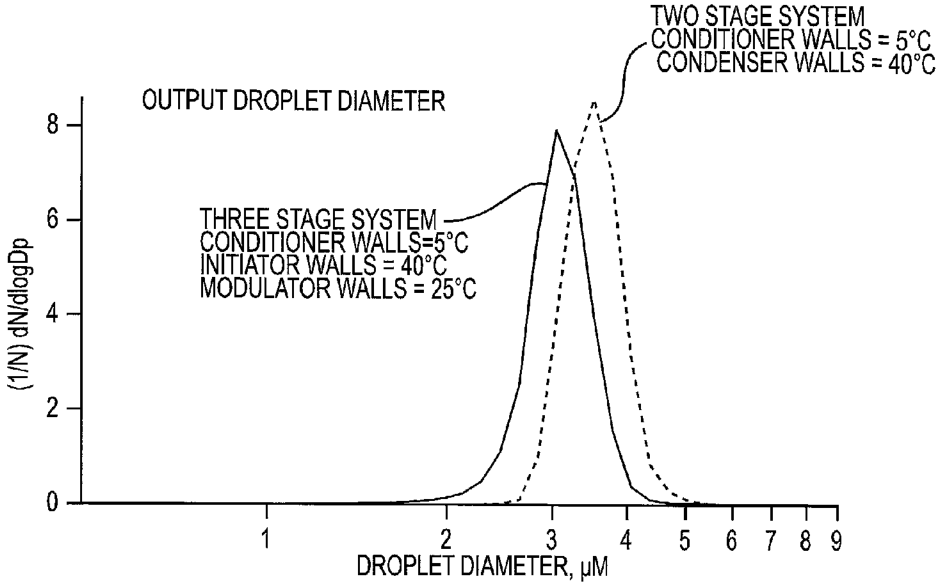
FIG. 7. is a graph illustrating a comparison of the size distribution of droplets formed for two- and three-stage systems in accordance with the present invention.

As illustrated in FIG. 7, the droplets formed by the 3-stage approach used in the "smart sampler" are only slightly smaller than the droplets formed by the two-stage approach, and are still readily collected by inertial methods. The data illustrated are for the two-stage system and a three-stage system of the geometry, and operated with the same temperature for the first stage, and the same temperature jump when transitioning to the warm, second stage (the overall droplet size is larger than for FIG. 6, because the temperature jump at the junction into the warm, wet walled section is greater).

Figure 8A:
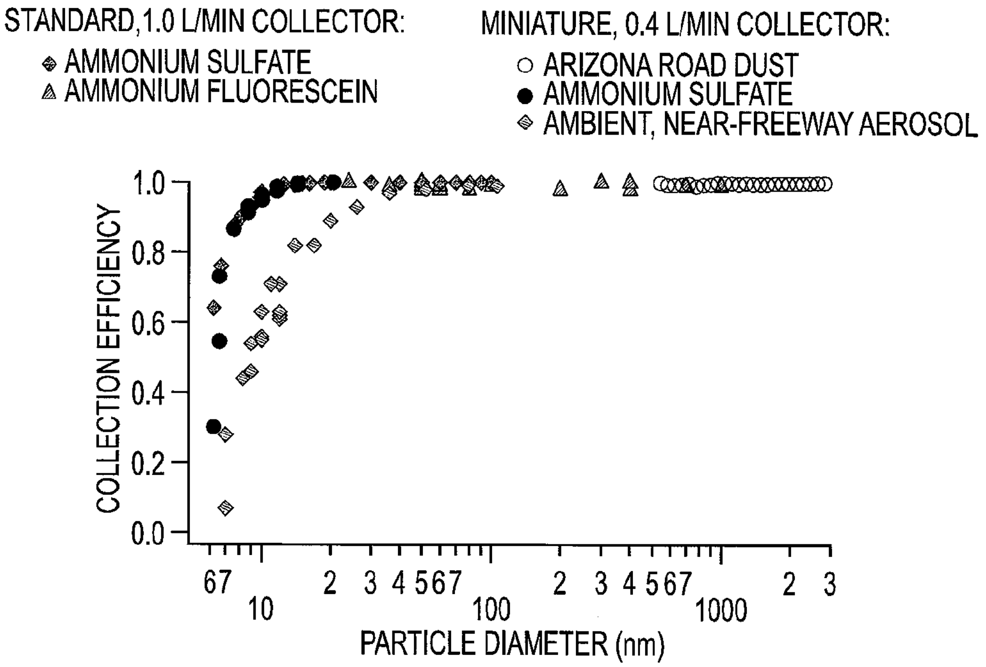
FIG. 8A. is a graph illustrating collection efficiency as a function of particle size for two, two-stage impaction based collector systems in accordance with the present invention.
Figure 8B:
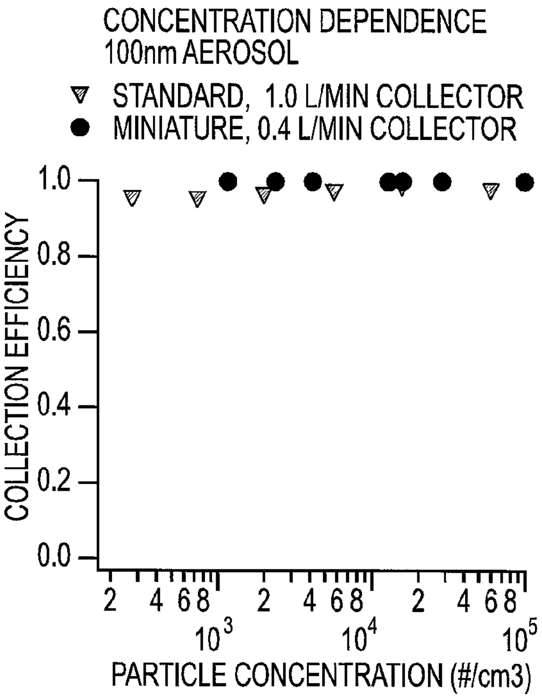
FIG. 8B is a graph illustrating collection efficiency as a function of particle number concentration for laboratory-generated 100-nm oleic acid aerosols for the systems of FIG. 8A in accordance with the present invention.

Referring now to FIGS. 8A and 8B, FIG. 8A in particular illustrates the size dependent collection efficiency of the two-stage system of FIG. 1. Also illustrated are data from a larger system, but with similar design, these curves are characterized by their lower cutpoint, defined as the size at which the collection efficiency is 50%. For ammonium sulfate aerosols, the lower cutpoint is about 6 nm. For ambient particles sampled near a freeway, the lower cutpoint is about 10 nm. Tests with Arizona road dust show essentially 100% collection efficiency for particles as large as 3 μm. In addition, FIG. 8B shows the collection efficiency for 100 nm particles as a function of the number concentration of the particles sampled. This was examined to ensure that the performance of the system does not degrade at high concentrations. As illustrated, the efficiency remains high for concentrations at least up to $10^6$ $cm^{-3}$.

Figure 9A:
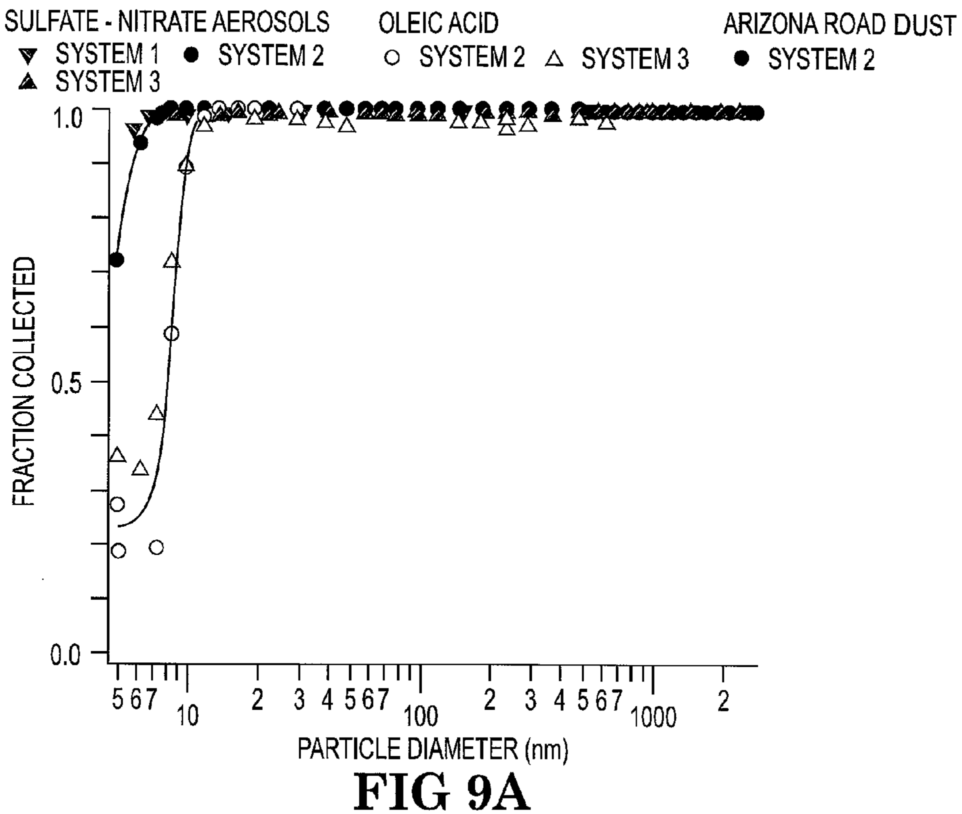
FIG. 9A. is a graph illustrating collection efficiency as a function of particle size for the three-stage multi-well collector system illustrated in FIG. 3A in accordance with the present invention.
Figure 9B:
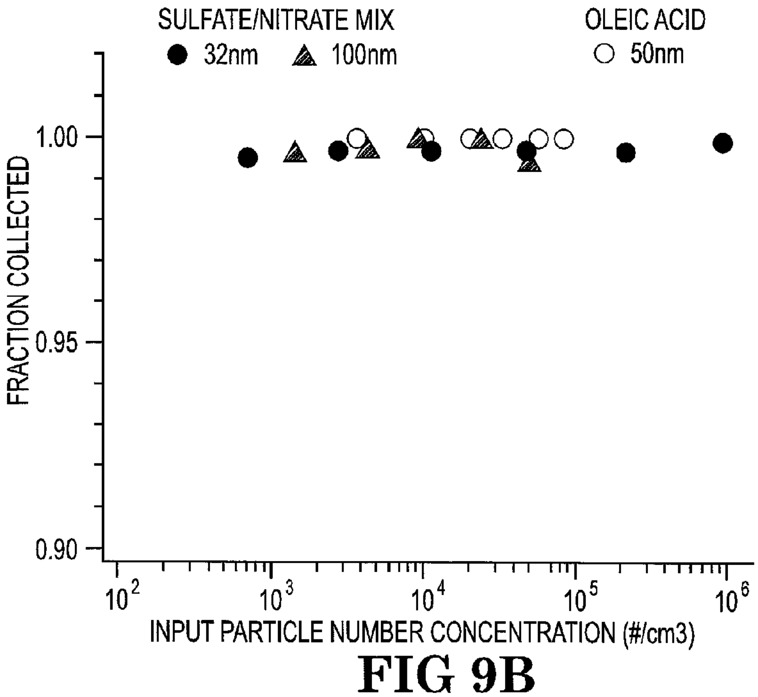
FIG. 9B. is a graph illustrating collection efficiency at two particle sizes, as a function of particle number concentration the systems of FIG. 9A in accordance with the present invention.

Referring now to FIGS. 9A-9B, FIG. 9A in particular illustrates the size dependent collection efficiency of the three-stage systems of FIGS. 3A-3B. Collection is by impaction into the multi-well plate or surface, forming a dry deposit. The test aerosol is ammonium sulfate generated through atomization and size selected using a high-flow differential mobility analyzer. A particle counter was located upstream to measure particle number concentration of the aerosol and another counter was located downstream from the sampling system to measure concentration of particles that were not collected. An optical counter (UHAS, Droplet Measurement Technologies) was also used to confirm particle size and determine fraction of larger, multiply charged particles. The lower cutpoint is below 6 nm. For particles larger than 8 nm the collection efficiency is above 99%. Tests with 32 and 100 nm aerosol at concentrations as high as $10^6$ $cm^{-3}$ are illustrated in FIG. 9B. There is no degradation in performance with increased particle number concentration. FIG. 9A illustrates the collection efficiency for particle sizes from 7 nm to 2.5 μm.

Figure 10:
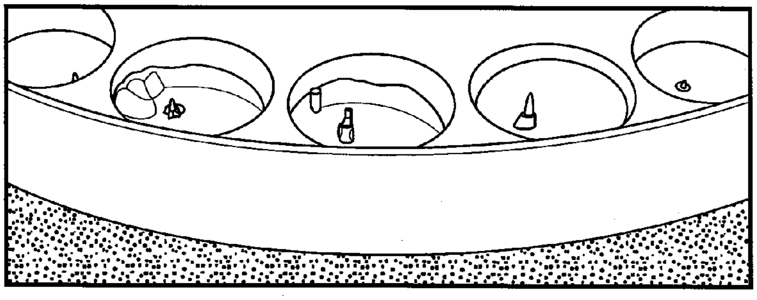
FIG. 10. is a collection of deposits formed by sampling Arizona road dust with the multi-well collection system of FIG. 3. For purposes of scale, the individual wells are 6 mm in diameter and 2 mm deep in accordance with the present invention.

A further advantage of the collection devices described herein is the elimination of particle bounce in collection by impaction. Generally impaction, especially for small particles, requires high jet velocities. This in turn leads to the rebound of particles upon contact with the surface, such that they are not collected. While not a problem for liquid particles, such as wetted particles or oils, it is well known for solid particles and dry dusts. Often collection efficiencies for dry particles are reduced significantly due to bounce. However, as the nanomaterial collector impacts the particles as droplets, they do not bounce. Indeed, we observe that when sampling dry road dust through the growth tube it will form small piles of particles under the impaction jet, as illustrated in FIG. 10.

Figure 11:
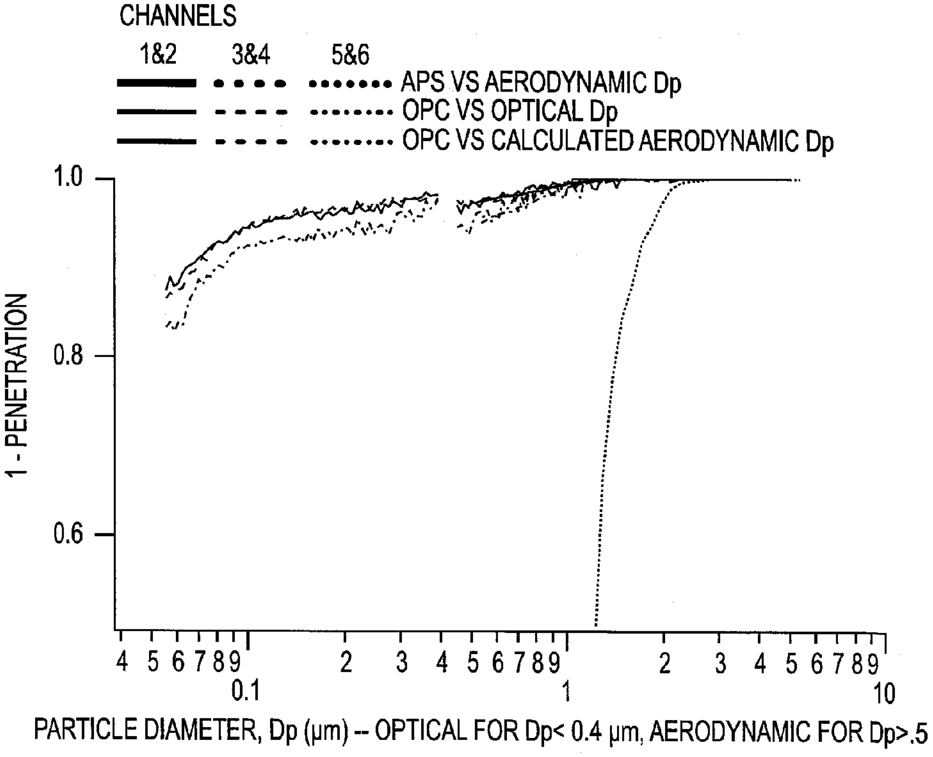
FIG. 11. is a graph illustrating collection efficiency as a function of particle size for the two-stage, parallel plate configuration using a cyclone collector, as illustrated in FIG. 2 in accordance with the present invention.

Referring now to FIG. 11, there is illustrated the collection efficiency measured for the high-flow, parallel plate system of FIG. 2, which utilizes a cyclone collector. Here the data extend from 50 nm to 10 μm. All sizes above 100 nm show collection efficiencies of 90% or greater. Also illustrated is the collection efficiency attained with the cyclone alone, without the growth system, which is essentially zero for particles below 1 μm.

The "smart sampler" (devices 300A and 300B) has been used for measuring atmospheric concentrations of particle bound sulfate, nitrate and selected polycyclic aromatic hydrocarbons (PAH). Its suitability for chemical analysis has been evaluated through laboratory studies with sulfate and nitrate aerosols. The mass of inorganic ion within each collection well was measured using a Dionex IC-2100 system (Dionex, Sunnyvale, Calif.), consisting of an AS autosampler, an eluent generator (KOH in our case), a continuous regenerating trap, a self-regenerating suppressor unit, an AS18 column-guard and column, and an electrochemical detector. For analysis, the collection plate or surface is placed in the autosampler as illustrated in FIG. 5. The autosampler is programmed to handle the steps of dispensing the preparation solution, triggering the rotation of the plate or surface, cleaning the needle and injection the sample through a six-port valve. For the data illustrated, the autosampler dispenses 80 uL of the preparation solution (Milli-Q water and dichloroactetate as internal standard) and the sample is allowed to soak for 30 min prior to injecting 20 uL of the extraction solution. Experimental evaluation showed that 30 min soaking time was enough to extract 90-99% of the sulfate and nitrate associated with the particles. By programming the autosampler to dispense two samples ahead of the one to be injected, the sample soaking time overlaps with the chromatograph run time of the previous two samples, allowing automated analysis of 4 samples per hour. Standards are added directly to the well plate, and analyzed as part of the same protocol. Analyte separation was obtained using a gradient mobile phase starting at 20 mM KOH To assess reproducibility, a stable laboratory generated aerosol of ammonium sulfate and ammonium nitrate was generated, and a total of six consecutive samples of 5 min and 30 min were collected on a multi-well PEEK plate. The plate was placed on the AS autosampler and nitrate and sulfate concentrations measured as described above. The standard deviation (STDEV) for each set of runs, expressed as a percentage of the mean, is illustrated on Table 1. Good precision was obtained for the sampling and analysis systems with standard deviation of less than 6% of the mean concentration. Higher variation was observed for the nitrate probably due to the higher volatility of this species.

TABLE 1

Standard deviation for the collection and analysis system

| | 5 min (n = 6) | 30 min (n = 6) |
|---|---|---|
| Sulfate (STDEV) | 4.21% | 3.52% |
| Nitrate (STDEV) | 5.36% | 4.25% |

Figure 12:
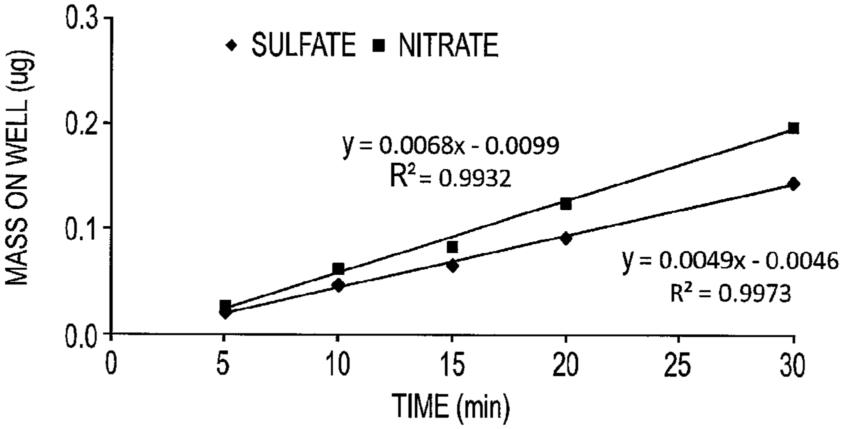
FIG. 12. is a graph illustrating linearity for measurement of sulfates and nitrate ions in accordance with the present invention.

To assess linearity, the sample collection time for the laboratory test aerosol was varied from 5 min to 30 min in a step wise manner. Results, reported as mass of analyte on the well for a given sampling time, are illustrated on FIG. 12. Correlations larger than 0.99 were obtained for both analytes. These high correlations suggest that no volatilization of compounds occurs for sample collections up to 30 minutes.

Figure 13:
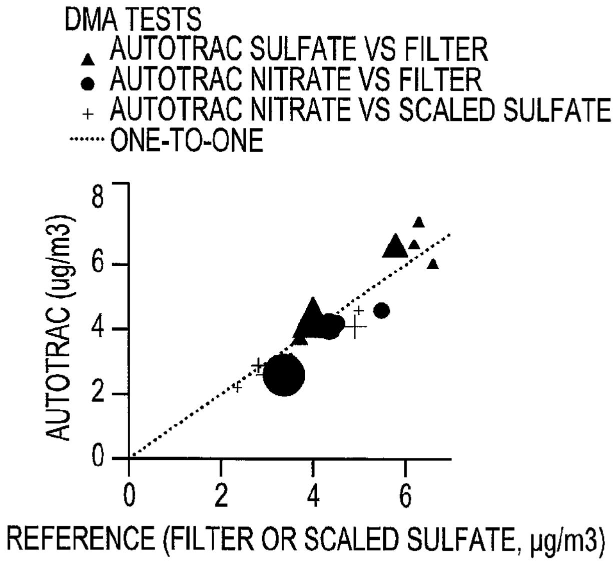
FIG. 13. is a graph illustrating evaluation of nitrate losses relative to sulfate for sampling of filtered air after an initial particle collection in accordance with the present invention.

Tests of sample integrity were conducted with ammonium nitrate, a volatile aerosol constituent that is readily lost during filter collection. Tests were done with laboratory generated, 100-nm particles comprised of ammonium nitrate and ammonium sulfate. Some samples were removed immediately after collection. Others were left with filtered air flowing into the sampler inlet and across the deposit for another 2, 5 or 11 hours, respectively. Results are illustrated in FIG. 13, which compares the measured nitrate on the exposed samples to the measured sulfate multiplied by the nitrate/sulfate concentration ratio measured in the nebulizer solution. The size of the sample is proportional to the length of filtered air exposure. The sulfate concentrations provide a reference value for the nitrate, which can be lost by volatilization, under the generally-accepted assumption that the sulfate is stable. Measured losses for the 5- and 11-hr exposures were about 10%. Two factors limiting loss during sampling are the high relative humidity at collection, which reduces nitrate volatility, and the overall lower loss for impactor sampling vs. filter sampling.

Figure 14:
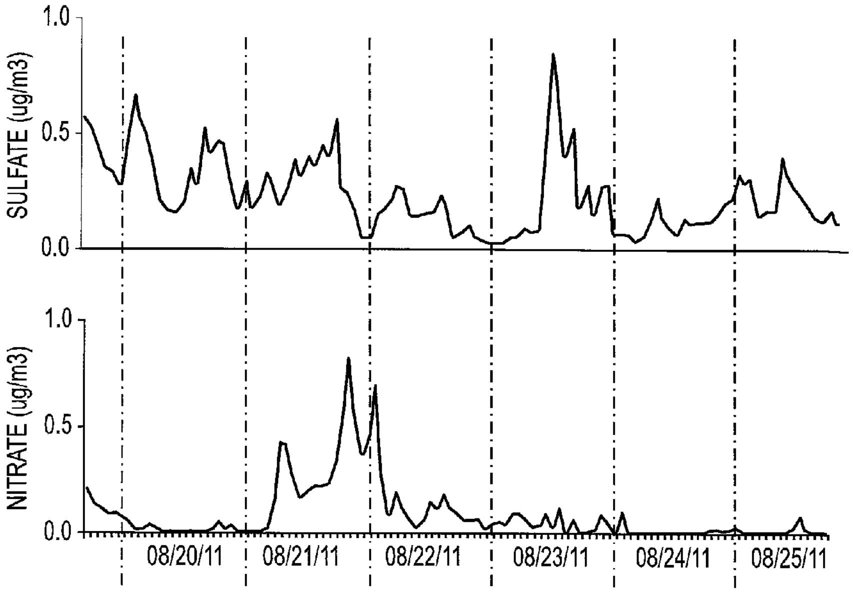
FIG. 14. is a graph illustrating time series of hourly sulfate and nitrate concentrations measured in ambient air in Berkeley, Calif. in accordance with the present invention.

In another experiment, hourly ambient concentrations of sulfate and nitrate were measured in Berkeley, Calif. with the smart sampler (device 300) as illustrated in FIG. 14. These time series, show 1-hour time resolution over a period of one week. During the sampling week, the autosampler ran unattended for 24-hours, and personnel involvement was only required once a day when changing the collection plates. The well collection plates have been designed to contain 24-wells which could allow collecting hourly samples for diurnal patterns. If longer periods of time are used for collection, i.e. 24-hr samples, the personnel requirement could be even less (once every month). Alternatively, the sample plate or surface can be reconfigured to provide for additional collection wells.

The performance of the smart sampler (e.g., 300A) for analysis of polycyclic aromatic hydrocarbons was tested through deployment of a pair of samplers in Stockton, Calif. Because of the toxicity of these compounds, tests were done in the field rather than in the laboratory. Accuracy was assessed using a filter as a reference. Precision was assessed using co-located samplers. Airborne particles with diameters less than 2.5 μm aerodynamic diameter (called $PM_{2.5}$) were collected every 12-hours over a 3-month period from Nov. 11, 2011 to Feb. 7, 2012. The systems ran unattended for period one week at a time. Parallel filters were also collected to assess sampler collection efficiency and sampling artifacts. Following a successful automation of the analytical method for ion analysis, similar steps were conducted to develop a new automated method for the analysis of polycyclic aromatic hydrocarbons (PAHs) using High Performance Liquid chromatography with Fluorescence detection (HPLC-FL). The addition of a 20-sec sonication step during the analysis improves the overall extraction efficiency of these compounds by 20%. With this approach we can quantitate 15-PAHs in air volumes as small as 1 $m^3$ without preconcentration or prefractionation steps.

Figure 15A:
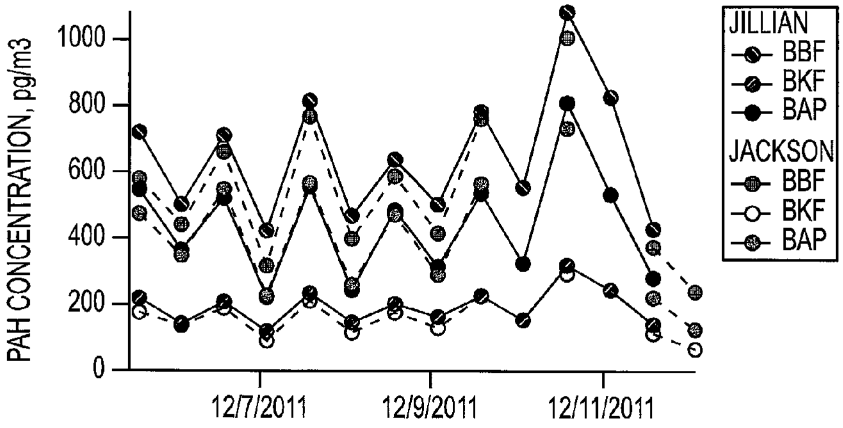
FIGS. 15A-15C. are graphs illustrating time series for co-located samplers measuring 8 different polycyclic aromatic hydrocarbons in Stockton, Calif. "Jillian" and "Jackson" refer to each of two co-located samplers. The 8 different polycyclic aromatic hydrocarbon compounds are referred to by their abbreviations, where BBF is benzo-b-fluoranthene, BKF is benzo-k-fluoranthene, BAP is benzo-a-pyrene, PYR is pyrene, CRY is chrysene, PHE is phenanthrene, ANT is anthracene, FLT is fluoranthene in accordance with the present invention.
Figure 15B:
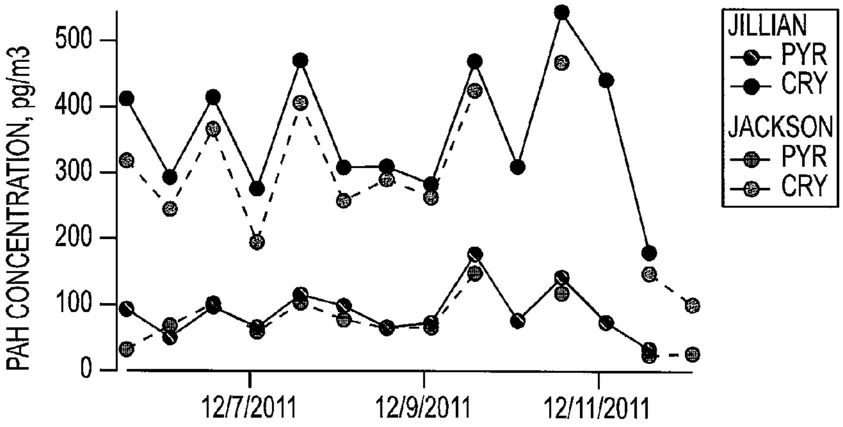
Figure 15C:
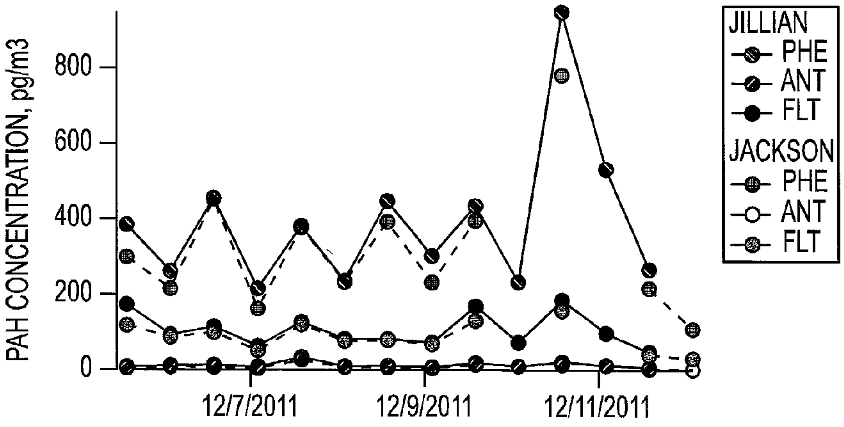
Figure 16:
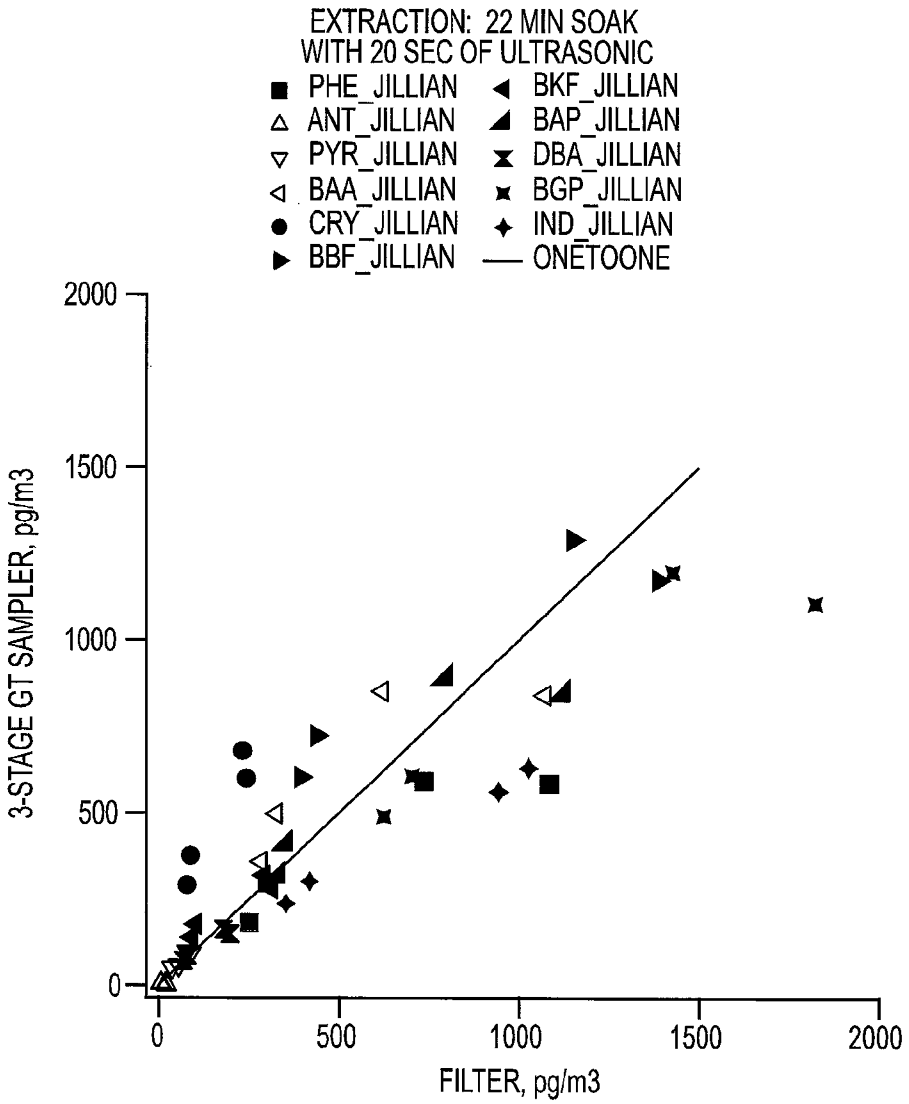
FIG. 16. is a graph illustrating comparison to parallel filter measurements for 11 polycyclic aromatic hydrocarbon compounds. BBF is benzo-b-fluoranthene, BKF is benzo-k-fluoranthene, BAP is benzo-a-pyrene, PYR is pyrene, CRY is chrysene, PHE is phenanthrene, ANT is anthracene, and FLT is fluoranthene. DBA is dibenzoantracene, BGP is benzo-g-perylene, IND is indenopyrene in accordance with the present invention.

Good precision and reproducibility were observed for the parallel smart sampler systems ("Jillian" and "Jackson) over the period of study for 8 polycyclic aromatic hydrocarbons (as illustrated in FIG. 15), with coefficients of variation ranging from 7% for the benzo[a]pyrene to 30% for anthracene. The 8 different polycyclic aromatic hydrocarbon compounds are referred to by their abbreviations, where BBF is benzo-b-fluoranthene, BKF is benzo-k-fluoranthene, BAP is benzo-a-pyrene, PYR is pyrene, CRY is chrysene, PHE is phenanthrene, ANT is anthracene, FLT is fluoranthene. Coefficients of variation were higher for lower molecular weight compounds which partition between the vapor- and particle-phase, and are more prompt to undergo evaporation loses during sampling. Total PAH concentrations measured with smart sampler collection system 300 vary between 80-110% of those found on 48-hr filter collections (as illustrated in FIG. 16). For individual PAHs BBF is benzo-b-fluoranthene, BKF is benzo-k-fluoranthene, BAP is benzo-a-pyrene, PYR is pyrene, CRY is chrysene, PHE is phenanthrene, ANT is anthracene, and FLT is fluoranthene, better agreement was observed for compounds mostly found in the particle-phase; as 48-hr filters are subjected to sampling artifacts.

Figure 17:
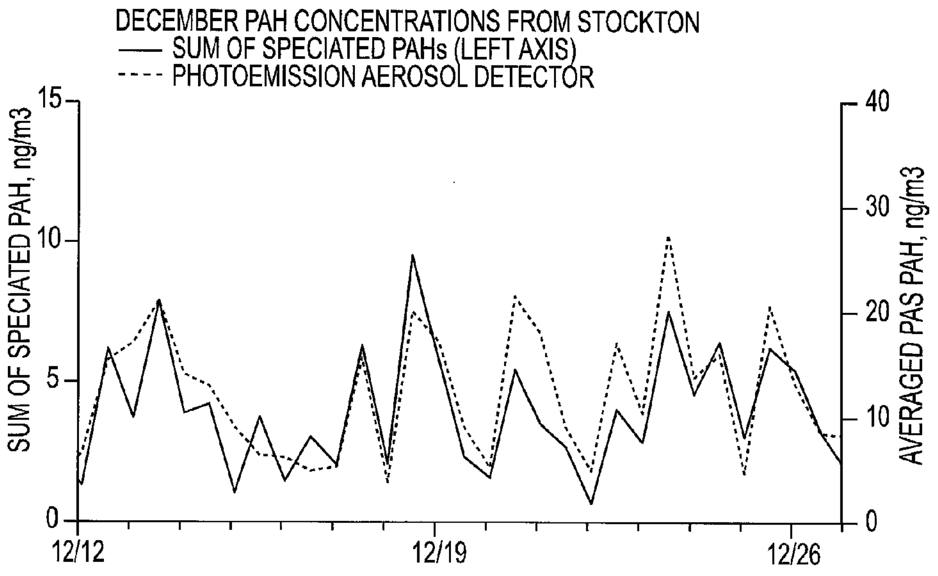
FIG. 17. is a graph illustrating time series of the sum of speciated polycyclic aromatic hydrocarbons (PAHs) and inferred total PAH concentration from a photoemission aerosol sensor in accordance with the present invention.
Figure 18:
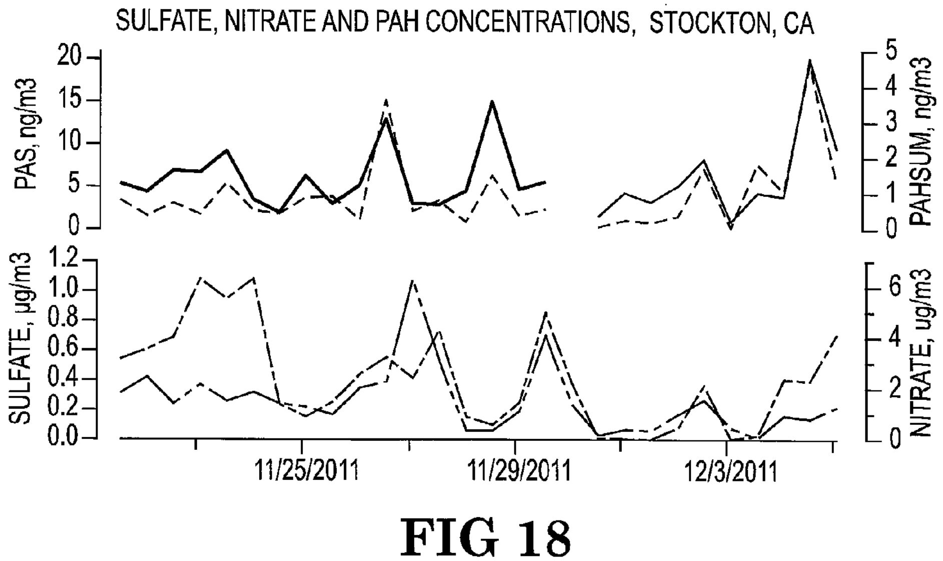
FIG. 18. is a graph illustrating time series of the sum of speciated polycyclic aromatic hydrocarbons (PAHs) and of sulfate and nitrate from parallel samplers in accordance with the present invention.

FIG. 17 illustrates a time series of the sum of speciated PAHs and inferred total PAH concentration from a photoemission aerosol sensor. With a 12-hr time-resolution afforded by sampler device 300, we observed a clear day/night pattern in the ambient PAH concentrations. In general, nighttime concentrations were higher than daytime values (as illustrated in FIG. 17). An increase in ambient PAH concentrations was observed during the Christmas Holidays, when contributions from fireplaces added up to the common emission sources. Diurnal and temporal variations are important when determining contribution of emission sources to ambient pollutants as well as assessing human exposure. The temporal variability of total PAH concentrations observed with our collection system tracked the diurnal pattern measured simultaneously by an EcoChem PAS-2000 photoemission aerosol sensor, which is generally considered an indicator of PAH concentration. This similarity with another widely used near-real system supports the validity of the collector systems disclosed herein. In FIG. 18, there is an illustrated result from parallel samplers, one of which was analyzed for speciated polycylic aromatic hydrocarbons, and the other of which was analyzed for inorganic ions.

Figure 19:
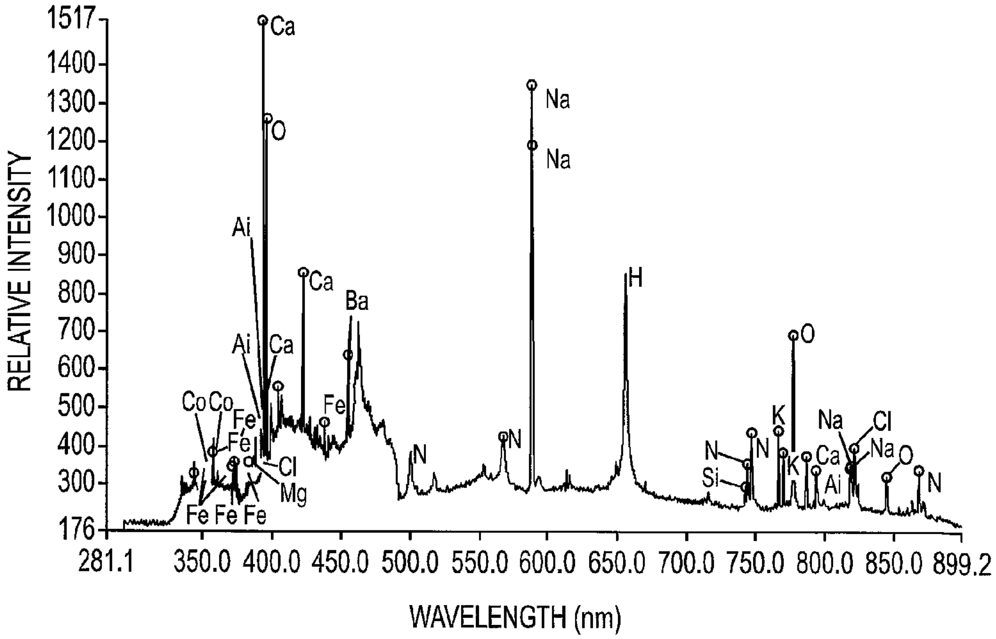
FIG. 19 is an example spectra for a sample analyzed for elemental composition measured by LIBS in accordance with the present invention.

The inorganic ion and polycyclic aromatic hydrocarbon analyses presented above are just examples of the range of chemical composition that can be measured with the nanomaterial particle collection methods of this disclosure. Many other types of constituents of airborne particles may be measured. FIG. 19 illustrates a spectrum obtained by Laser Induced Breakdown Spectroscopy (LIBS) from one of the samples ($PM_{2.5}$), indicating that elemental analysis is possible. Other possibilities include assessment of the toxicity of airborne particles through direct dosing of live cells by using the various embodiments of the nanomaterial particle collectors taught herein to deposit airborne particles directly onto a layer of cells. Concentrated collection onto an agar medium or other culture media for bioaerosol measurement is also possible. The flexibility of the various embodiments of the nanomaterial particle collector taught herein is such that the collection substrate and the collection temperature and relative humidity can be controlled to the desired end point for the analysis at hand. For example, collection at approximately 37° C. is possible for biological assays. Similarly, collection at a reduced temperature of about 10° C. could also be an option if sample stability is of concern. These and many other variations are possible with this approach.

In one example experiment using a collector member, a 300 μm shot was fired at 100% laser energy and a spectrometer delay of 1 pico sec in each of a couple of the wells as well as on a portion of the plastic closest to the center of the disc collector and furthest from any of wells in each case creating a plasma to be analyzed by LIBS. After data was collected by way of the collected nanoparticles, the remaining particles were blown away by the plasma, leaving a black or bump spot or mark from the laser pulse on the plastic material of the disc collector. Various test shots were used to determine if an elemental composition different from the plastic material of the disc could be seen from the tiny deposits of particles. Elements of a composition different from that of the plastic were seen in the spectra taken from the two shots.

In a related example embodiment, a biological nanomaterial collection system conducts real time contamination monitoring in pharmaceutical processing clean areas. The system draws an air sample via an inlet using a pump and a conduit. Particles are eventually directed to a water-based collector device as discussed above in order that the particles are grown and then collected by a collection device (such as a collection plate or plate or surface). Once collected by some medium or device the collected particles are moved to a biological analytics station for analysis. In various related example embodiments, the biological nanomaterial collection system provides viable sampling of viruses, DNA, proteins and the like. In this example embodiment, a particle collector is configured for collection onto a viability preserving gel filter for post-analysis and confirmation of any real time viable particle detection and to preserve samples for biological species identification.

In another example embodiment of a nanoparticle collector member (or plate) according to the teachings of the invention, a collector member is formed in a half aluminum, half PEEK (plastic) disc configuration that includes a plurality of particle collection or capture wells or indentations disposed on the periphery of the disc member (see for example FIGS. 4A-4B). In related embodiments, the collector member is made of other geometric configurations (oval, rectangular, square, etc.) and of other materials and composites and is not limited to just one homogeneous material or combination of materials.

While the invention has been described in connection with certain preferred embodiments, there is no intent to limit it to those embodiments. On the contrary, it is recognized that various changes and modifications to the exemplary embodiments described herein will be apparent to those skilled in the art, and that such changes and modifications may be made without departing from the spirit and scope of the present invention. Therefore, the intent is to cover all alternatives, modifications and equivalents included within the spirit and scope of the invention as defined by the appended claims.

We claim:

1. A particle collection system, comprising:

a particle growth assembly having interior wetted walls and configured to receive a particle laden aerosol flow at a flow rate less than or equal to 100 L/min, the particle growth assembly including a condensing vapor having a vapor pressure at the interior walls which is near saturation, wherein the aerosol flow through the particle growth assembly is configured to be a laminar flow, the particle growth assembly including:

a conditioning portion with a wetted interior wall configured to bring the aerosol flow to near saturation at a first temperature (T1);

an initiator portion with a wetted interior wall operatively coupled to said conditioning portion and configured to provide supersaturation conditions at a second temperature (T2) for the aerosol flow using the condensing vapor to initiate droplet growth, wherein the second temperature (T2) is configured to be higher than the first temperature (T1); and a equilibrator portion with a wetted interior wall operatively coupled to said initiator portion and configured to lower a dew point for the aerosol flow and maintain supersaturation conditions for the aerosol flow at a third temperature (T3), wherein the third temperature (T3) is configured to be lower than the second temperature (T2);

a collection member for collecting by inertia the enlarged particles, the collection member positioned adjacent a nozzle member operatively coupled to an outlet of said particle growth assembly; and a displacement assembly adapted to displace the collection member under the particle growth assembly.

2. The system of claim 1 wherein the nozzle member is heated to prevent condensation from droplets including the enlarged particles.

3. The system of claim 1 wherein the collection member includes a collection plate with one or more collection wells formed therein in an x-y grid pattern, wherein the displacement assembly includes a stepper motor that moves the collection plate in an x-y grid pattern under the nozzle member and receives enlarged particles from the nozzle member.

4. The system of claim 1 wherein the displacement assembly includes a stepper motor adapted to displace the collection member under the particle growth assembly and under the nozzle member, wherein the collection member includes a circular collection plate having one or more collection wells at a periphery of the plate and wherein the stepper motor rotationally moves the plate such that each collection well receives enlarged particles from the nozzle member.

5. The system of claim 1 wherein the particle growth assembly is substantially tubular in shape and includes a wick member extending from said conditioner through said initiator and through said equilibrator.

6. The system of claim 1 further comprising a mechanism for controlling a temperature of the collection member and wherein the temperature controlling mechanism is operatively coupled to the collection member to evaporate fluid as the enlarged particles and droplets are deposited.

7. The system of claim 1 wherein the collection member includes at least one from the group consisting of impaction assembly and a cyclone assembly.

8. The system of claim 1 further comprising an autosampler system configured to analyze the particles in the collection member.

9. The system of claim 1 wherein a shape of the particle growth assembly is substantially tubular in geometry.

10. The system of claim 1 further including an optical device for detecting particulate exiting the condenser.

11. The system of claim 1 wherein a geometric shape of the particle growth assembly includes a parallel plate configuration.

12. The system of claim 1 wherein a mass diffusivity of the condensing vapor is larger than or about equal to the thermal diffusivity of a carrier gas.

13. A method for collecting and concentrating particles for use in characterizing such particles in an aerosol flow comprising the steps of:

introducing a particle laden flow at a flow rate less than or equal to 100 L/min at a first temperature into a condenser;

passing the flow through the condenser having a second temperature greater than the first temperature flow wherein a vapor pressure of a condensing vapor at walls of the condenser is near saturation, thereby enlarging the particles to be collected;

collecting by inertia the enlarged particles unto a collection member having formed therein one or more collection wells; and displacing with a stepper motor the collection member under a nozzle member coupled to the condenser.

14. The method of claim 13 further comprising controlling a temperature of the collection member so as to evaporate fluid as the enlarged particles and droplets are deposited.

15. The method of claim 13 wherein the step of displacing the collection member includes rotationally moving a circular collection plate having one or more collection wells at a periphery of the plate such that each collection well receives enlarged particles from the nozzle member.

16. The method of claim 13 wherein the step of displacing the collection member includes moving a collection plate, having the collection wells formed in an x-y grid pattern, in an x-y pattern such that each collection well receives enlarged particles from the nozzle member.

17. The method of claim 13 wherein the step of introducing the particle-laden flow includes conditioning a temperature and vapor pressure of the particle-laden flow.

18. The method of claim 13 further comprising the step of heating the nozzle member to reduce condensation.

19. The method of claim 18 further comprising the step of conditioning a temperature of the collected particles by impaction.

20. The method of claim 13 wherein the step of collecting the particles by inertia includes collection by impingement or impaction.

21. The method of claim 20 further comprising the step of conditioning a temperature of the collected particles by impingement.

22. The method of claim 13 wherein the step of introducing the particle-laden flow comprises actively cooling the flow such that the first temperature is at least 15° C. lower than the second temperature.

23. The method of claim 13 wherein the step of introducing the particle-laden flow comprises actively cooling the flow such that the first temperature is at least 25° C. lower than the second temperature.

24. The method of claim 13 wherein the step of introducing the particle-laden flow comprises actively cooling the flow such that the first temperature is at least 45° C. lower than the second temperature.

25. The method of claim 13 wherein a mass diffusivity of the condensing vapor is larger than or about equal to the thermal diffusivity of a carrier gas.

26. A particle collection apparatus, comprising:

an inlet receiving a particle laden aerosol flow at a flow rate less than or equal to 100 L/min;

a condenser coupled to the inlet and receiving the aerosol flow at a first temperature, the condenser having interior walls provided at a second temperature higher than the first temperature and including a condensing vapor having a vapor pressure at the interior walls which is near saturation, wherein the condenser is comprised of parallel plate configuration adapted for a laminar lateral flow of the particle laden flow; and a collection member for collecting by inertia the enlarged particles, the collection member positioned adjacent a nozzle member operatively coupled to an outlet of the condenser; and a displacement assembly adapted to displace the collection member under the condenser and disposed near an outlet of the condenser.

27. The apparatus of claim 26 further comprising a preconditioner at the first temperature and being coupled to the inlet, the preconditioner having an outlet coupled to the condenser.

28. The apparatus of claim 27 further including an autosampler system configured to analyze the particles in the collection member.

29. The apparatus of claim 26 wherein a geometric shape of the condenser is of a tubular configuration.

30. The apparatus of claim 26 wherein the condensing vapor is water.

31. The apparatus of claim 26 wherein the collection member includes at least one from the group consisting of impaction assembly and a cyclone assembly.

32. The apparatus of claim 26 wherein the first temperature is at least 15° C. lower than the second temperature.

33. The apparatus of claim 26 wherein the first temperature is at least 25° C. lower than the second temperature.

34. The apparatus of claim 26 further including an optical device for detecting particulate exiting the condenser.

35. The apparatus of claim 26 wherein displacement assembly includes a rotating assembly adapted to rotate the collection member under the condenser.

36. The apparatus of claim 26 further comprising a mechanism for controlling a temperature of the collection member, wherein said temperature controlling mechanism is operatively coupled to the collection member.

* * * * *